(12) United States Patent
Sidransky et al.

(10) Patent No.: US 10,801,071 B2
(45) Date of Patent: Oct. 13, 2020

(54) TGF(β)-MIR200-MIG6 PATHWAY AND ITS USE IN THE TREATMENT OF CANCER AS AN INDICATOR OF RESISTANCE TO EGFR INHIBITORS

(71) Applicant: THE JOHNS HOPKINS UNIVERSITY, Baltimore, MD (US)

(72) Inventors: David Sidransky, Baltimore, MD (US); Eugene Izumchenko, Baltimore, MD (US)

(73) Assignee: The Johns Hopkins University, Baltimore ( * ) Notice: Subject to any disclaimer, the term of this patent is extended or adjusted under 35 U.S.C. 154(b) by 0 days.

(21) Appl. No.: 15/305,750

(22) PCT Filed: Apr. 22, 2015

(86) PCT No.: PCT/US2015/026986
§ 371 (c)(1),
(2) Date: Oct. 21, 2016

(87) PCT Pub. No.: WO2015/164448
PCT Pub. Date: Oct. 29, 2015

(65) Prior Publication Data
US 2017/0175201 A1    Jun. 22, 2017

Related U.S. Application Data

(60) Provisional application No. 61/982,417, filed on Apr. 22, 2014.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/178* (2013.01)

(58) Field of Classification Search
None
See application file for complete search history.

(56) References Cited

U.S. PATENT DOCUMENTS

2013/0018088 A1    1/2013  Adam et al.
2013/0190310 A1    7/2013  Sidransky et al.

FOREIGN PATENT DOCUMENTS

WO    2012174282 A2    12/2012

OTHER PUBLICATIONS

Cobb et al (Crit Care Med 2002 vol. 30 p. 2711 (Year: 2002).*
Enard et al. (Science 2002 vol. 296 p. 340) (Year: 2002).*
Adam et al., (2009) "miR-200 expression regulates epithelial-to-mesenchymal transition in bladder cancer cells and reverses resistance to epidermal growth factor receptor therapy" Clinical Cancer Research, vol. 15, No. 16, pp. 5060-5072.
Chang et al., (2013) "The relative expression of Mig6 and EGFR is associated with resistance to EGFR kinase inhibitors" PloS One, vol. 8, No. 7, p. e68966 (Internal pp. 1-10).
Izumchenko et al., (2014) "The TGFβ-miR200-MIG6 pathway orchestrates the EMT-associated kinase switch that induces resistance to EGFR inhibitors" Cancer Research, vol. 74, No. 14, pp. 3995-4005 (Epub. May 15, 2014).
Chang, et al., The relative expression of Mig6 and EGFR is associated with resistance to EGFR kinase inhibitors. PLoS One. Jul. 31, 2013;8(7):e68966.
Adam, et al., miR-200 expression regulates epithelial-to-mesenchymal transition in bladder cancer cells and reverses resistance to epidermal growth factor receptor therapy. Clin Cancer Res. Aug. 15, 2009;15(16):5060-72.
Izumchenko, et al., The TGFβ-miR200-MIG6 pathway orchestrates the EMT-associated kinase switch that induces resistance to EGFR inhibitors. Cancer Res. Jul. 15, 2014;74(14):3995-4005.
Ferby, et al., Mig6 is a negative regulator of EGF receptor-mediated skin morphogenesis and tumor formation. Nat Med. May 2006;12(5):568-73.
Jimeno, et al., Coordinated epidermal growth factor receptor pathway gene overexpression predicts epidermal growth factor receptor inhibitor sensitivity in pancreatic cancer. Cancer Res. Apr. 15, 2008;68(8):2841-9.
Harsha, et al., Activated epidermal growth factor receptor as a novel target in pancreatic cancer therapy. J Proteome Res. Nov. 2008;7(11):4651-8.
Fiorini, et al., Expression of RALT, a feedback inhibitor of ErbB receptors, is subjected to an integrated transcriptional and post-translational control. Oncogene. Sep. 19, 2002;21(42):6530-9.
Lynch, et al., Activating mutations in the epidermal growth factor receptor underlying responsiveness of non-small-cell lung cancer to gefitinib. N Engl J Med. 2004;350:2129-39.
Paez, et al., EGFR mutations in lung cancer: correlation with clinical response to gefitinib therapy. Science. 2004;304:1497-500.
Tsao, et al., Erlotinib in lung cancer—molecular and clinical predictors of outcome. N Engl J Med. 2005;353:133-44.
Lemos-Gonzalez, et al., Absence of activating mutations in the EGFR kinase domain in Spanish head and neck cancer patients. Tumour Biol. 2007;28:273-9.
Tzeng, et al., Epidermal growth factor receptor (EGFR) is highly conserved in pancreatic cancer. Surgery. 2007;141:464-9.
Van Den Bent, et al., Randomized phase II trial of erlotinib versus temozolomide or carmustine in recurrent glioblastoma: EORTC brain tumor group study 26034. Journal of clinical oncology : official journal of the American Society of Clinical Oncology. 2009;27:1268-74.
Yauch, et al., Epithelial versus mesenchymal phenotype determines in vitro sensitivity and predicts clinical activity of erlotinib in lung cancer patients. Clinical cancer research : an official journal of the American Association for Cancer Research. 2005;11:8686-98.

(Continued)

*Primary Examiner* — Katherine D Salmon
(74) *Attorney, Agent, or Firm* — Johns Hopkins Technology Ventures

(57) ABSTRACT

The present invention provides methods for identifying the susceptibility of a cancer cell or population of cells to treatment with Epidermal Growth Factor (EGF) Tyrosine Kinase Inhibitors (TKIs), such as erlotinib. Methods for the in vitro diagnosis of the susceptibility of a tumor in a subject to treatment with TKIs and monitoring tumor susceptibility during treatment are also provided.

7 Claims, 14 Drawing Sheets

(56) References Cited

OTHER PUBLICATIONS

Thomson, et al., Kinase switching in mesenchymal-like non-small cell lung cancer lines contributes to EGFR inhibitor resistance through pathway redundancy. Clinical & experimental metastasis. 2008;25:843-54.
Barr, et al., Bypassing cellular EGF receptor dependence through epithelial-to-mesenchymal-like transitions. Clinical & experimental metastasis. 2008;25:685-93.
Massague, TGFbeta signalling in context. Nature reviews Molecular cell biology. 2012;13:616-30.
Vincent, et al., A SNAIL1-SMAD3/4 transcriptional repressor complex promotes TGF-beta mediated epithelial-mesenchymal transition. Nature cell biology. 2009;11:943-50.
Ozdamar, et al., Regulation of the polarity protein Par6 by TGFbeta receptors controls epithelial cell plasticity. Science. 2005;307:1603-9.
Samavarchi-Tehrani, et al., Functional genomics reveals a BMP-driven mesenchymal-to-epithelial transition in the initiation of somatic cell reprogramming. Cell stem cell. 2010;7:64-77.
Korpal, et al., The miR-200 family inhibits epithelial-mesenchymal transition and cancer cell migration by direct targeting of E-cadherin transcriptional repressors ZEB1 and ZEB2. The Journal of biological chemistry. 2008;283:14910-4.
Gregory, et al., The miR-200 family and miR-205 regulate epithelial to mesenchymal transition by targeting ZEB1 and SIP1. Nature cell biology. 2008;10:593-601.
Tryndyak, et al., E-cadherin transcriptional down-regulation by epigenetic and microRNA-200 family alterations is related to mesenchymal and drug-resistant phenotypes in human breast cancer cells. International journal of cancer Journal international du cancer. 2010;126:2575-83.
Burk, et al., A reciprocal repression between ZEB1 and members of the miR-200 family promotes EMT and invasion in cancer cells. EMBO reports. 2008;9:582-9.
Fiorentino, et al., Inhibition of ErbB-2 mitogenic and transforming activity by RALT, a mitogen-induced signal transducer which binds to the ErbB-2 kinase domain. Mol Cell Biol. 2000;20:7735-50.
Hackel, et al., Mig-6 is a negative regulator of the epidermal growth factor receptor signal. Biol Chem. 2001;382:1649-62.
Anastasi, et al., Feedback inhibition by RALT controls signal output by the ErbB network. Oncogene. 2003;22:4221-34.

Zhang, et al., Inhibition of the EGF receptor by binding of MIG6 to an activating kinase domain interface. Nature. 2007;450:741-4.
Nakamura, et al., Different modes and qualities of tyrosine phosphorylation of Fak and Pyk2 during epithelial-mesenchymal transdifferentiation and cell migration: analysis of specific phosphorylation events using site-directed antibodies. Oncogene. 2001;20:2626-35.
Cicchini, et al., TGFbeta-induced EMT requires focal adhesion kinase (FAK) signaling. Experimental cell research. 2008;314:143-52.
Bedi, et al., Inhibition of TGF-beta enhances the in vivo antitumor efficacy of EGF receptor-targeted therapy. Molecular cancer therapeutics. 2012;11:2429-39.
Gregory, et al., An autocrine TGF-beta/ZEB/miR-200 signaling network regulates establishment and maintenance of epithelial-mesenchymal transition. Molecular biology of the cell. 2011;22:1686-98.
Xu, et al., Mesenchymal stem cells play a potential role in regulating the establishment and maintenance of epithelial-mesenchymal transition in MCF7 human breast cancer cells by paracrine and induced autocrine TGF-beta. International journal of oncology. 2012;41:959-68.
Bryant, et al., A microRNA gene expression signature predicts response to erlotinib in epithelial cancer cell lines and targets EMT. British journal of cancer 2012;106:148-56.
Ceppi, et al., Loss of miR-200c expression induces an aggressive, invasive, and chemoresistant phenotype in non-small cell lung cancer. Molecular cancer research : MCR. 2010;8:1207-16.
Derynck, et al., Synthesis of messenger RNAs for transforming growth factors alpha and beta and the epidermal growth factor receptor by human tumors. Cancer research. 1987;47:707-12.
Dickson, et al., Activation of growth factor secretion in tumorigenic states of breast cancer induced by 17 beta-estradiol or v-Ha-ras oncogene. Proceedings of the National Academy of Sciences of the United States of America. 1987;84:837-41.
Xu, et al., TGF-beta-induced epithelial to mesenchymal transition. Cell research. 2009;19:156-72.
Nieto, The ins and outs of the epithelial to mesenchymal transition in health and disease. Annual review of cell and developmental biology. 2011;27:347-76.
Thiery, et al., Epithelial-mesenchymal transitions in development and disease. Cell. 2009;139:871-90.
Brabletz, et al., The ZEB/miR-200 feedback loop—a motor of cellular plasticity in development and cancer? EMBO reports. 2010;11:670-7.

* cited by examiner

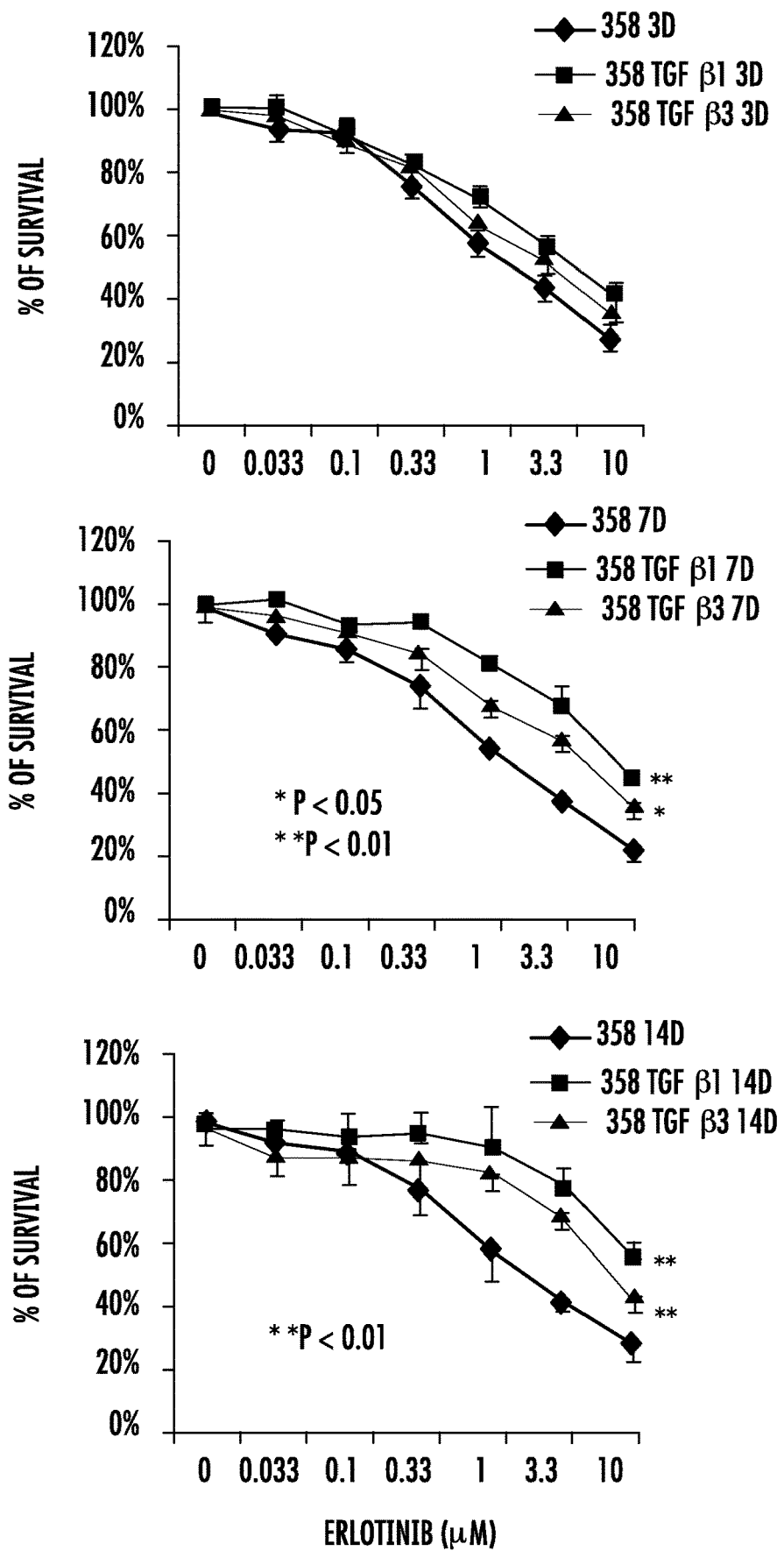

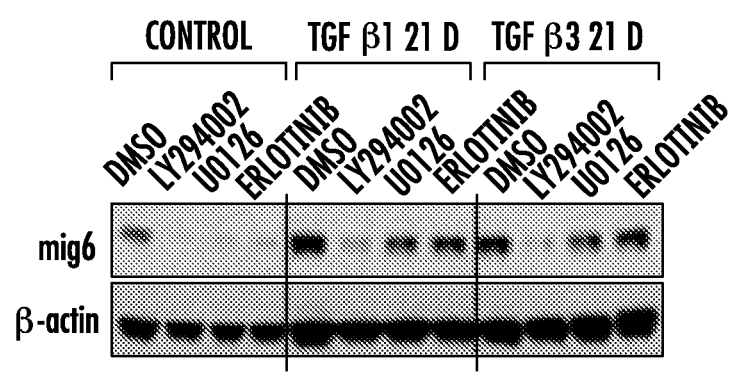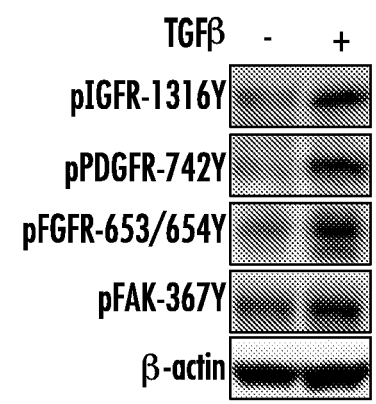
FIG. 2E
FIG. 2F

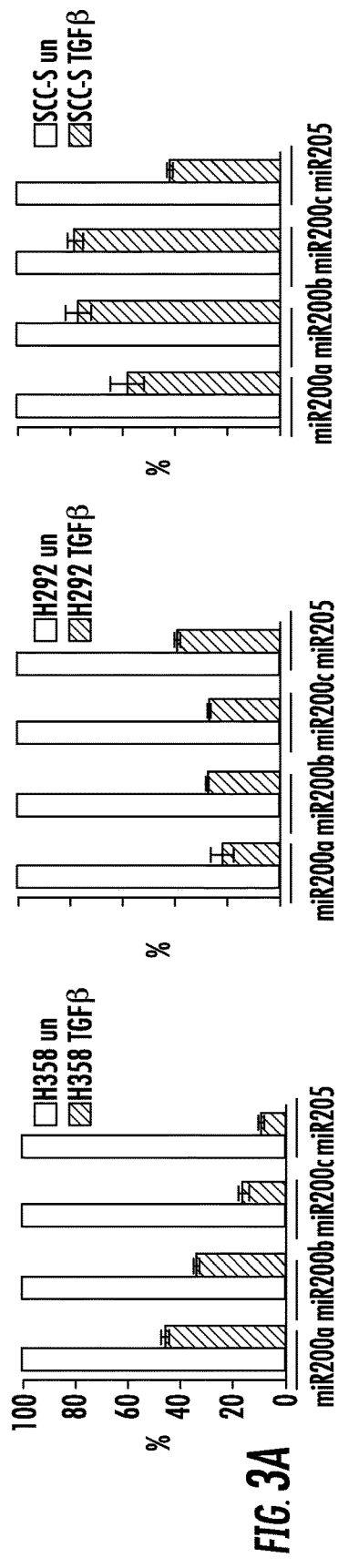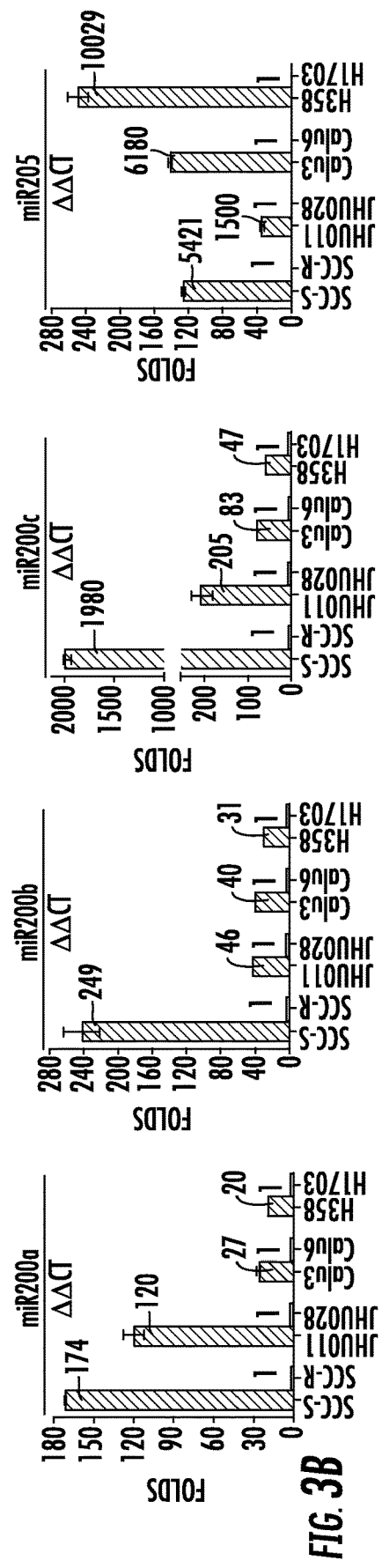
FIG. 3A
FIG. 3B

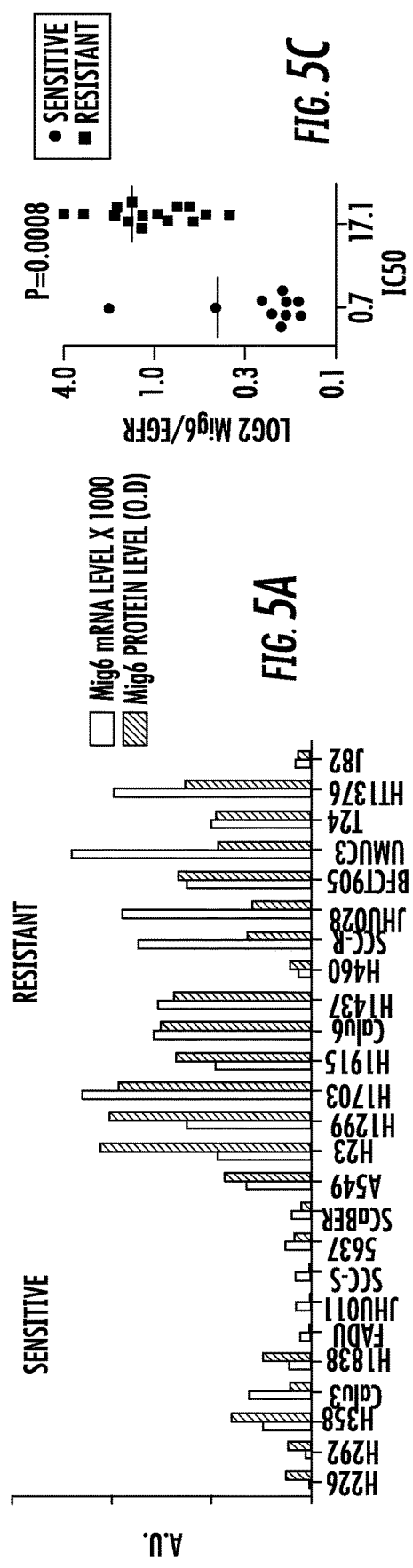
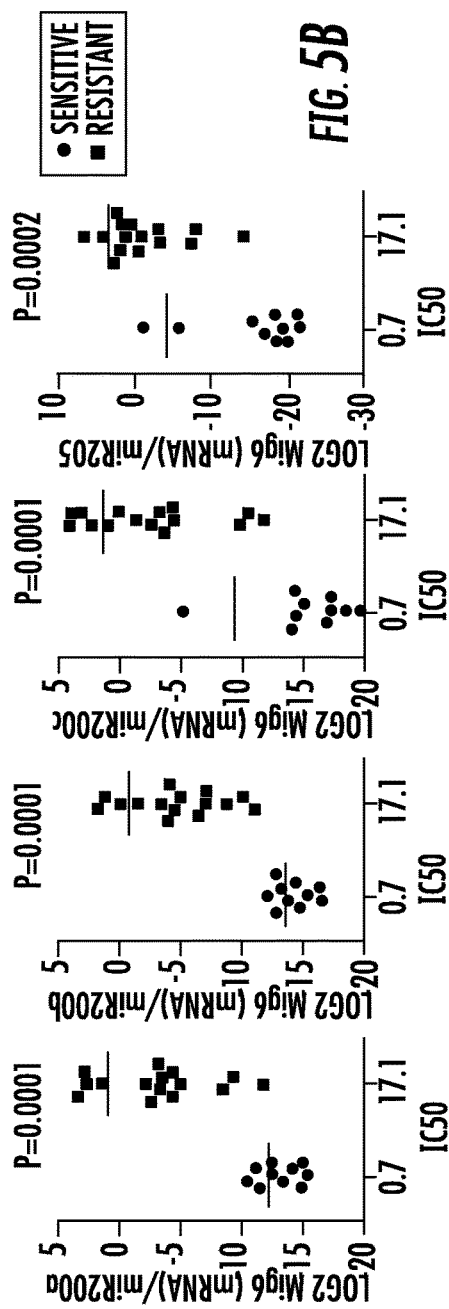
FIG. 5A
FIG. 5B
FIG. 5C

| # | MODEL NAME | TYPE | EGFR STATUS | KRAS STATUS | NRAS STATUS | p53 STATUS |
|---|---|---|---|---|---|---|
| 1 | CTG-0167 | LUNG NSCLC | WT | WT | WT | WT |
| 2 | CTG-0502 | LUNG NSCLC | WT | WT | WT | WT |
| 3 | CTG-0199 | LUNG NSCLC | WT | WT | WT | WT |
| 4 | CTG-0157 | LUNG NSCLC | WT | ND | ND | ND |
| 5 | CTG-0183 | LUNG NSCLC | WT | WT | WT | MUTANT R248L |
| 6 | CTG-0176 | LUNG NSCLC | WT | MUTANT G12C | WT | WT |
| 7 | CTG-0159 | LUNG NSCLC | WT | WT | WT | WT |
| 8 | CTG-0170 | LUNG NSCLC | WT | WT | WT | WT |
| 9 | CTG-0164 | LUNG NSCLC | WT | MUTANT G12V | WT | WT |
| 10 | CTG-0838 | LUNG NSCLC | WT | WT | WT | MUTANT R248L |
| 11 | CTG-0363 | LUNG NSCLC | WT | MUTANT G12D | WT | WT |
| 12 | CTG-0165 | LUNG NSCLC | WT | WT | WT | MUTANT FRAME SHIFT |
| 13 | CTG-0158 | LUNG NSCLC | WT | WT | WT | MISSENSE MUTATION-RETAINS WT FUNCTION |
| 14 | CTG-0178 | LUNG NSCLC | WT | WT | WT | WT |
| 15 | CTG-0765 | LUNG NSCLC | WT | WT | MUTANT Q61R | WT |
| 16 | CTG-0162 | LUNG NSCLC | WT | WT | WT | WT |
| 17 | CTG-0184 | LUNG NSCLC | WT | WT | WT | WT |
| 18 | CTG-0163 | LUNG NSCLC | WT | WT | WT | WT |

WT-WILD TYPE
ND-NOT DETERMINED

FIG. 8

| # | MODEL NAME | TYPE | EGFR STATUS | KRAS STATUS | NRAS STATUS | p53 STATUS |
|---|---|---|---|---|---|---|
| 1 | CTG-0727 | PANCREATIC | WT | MUTANT G12D | WT | MUTANT D208V |
| 2 | CTG-0285 | PANCREATIC | WT | MUTANT G12V | WT | WT |
| 3 | CTG-0286 | PANCREATIC | WT | MUTANT G12D | WT | MUTANT R306* |
| 4 | CTG-0282 | PANCREATIC | WT | WT | WT | WT |
| 5 | CTG-0851 | PANCREATIC | WT | ND | WT | ND |
| 6 | CTG-0492 | PANCREATIC | WT | MUTANT G12V | WT | WT |
| 7 | CTG-0299 | PANCREATIC | WT | WT | WT | WT |
| 8 | CTG-0288 | PANCREATIC | WT | MUTANT G12D | WT | MUTANT R273H |
| 9 | CTG-0305 | PANCREATIC | WT | MUTANT G12D | WT | WT |
| 10 | CTG-0314 | PANCREATIC | WT | MUTANT G12R | WT | MUTANT Y163C |
| 11 | CTG-0298 | PANCREATIC | WT | MUTANT G12D | WT | MUTANT M246V |
| 12 | CTG-0291 | PANCREATIC | WT | MUTANT G12D | WT | WT |
| 13 | CTG-0290 | PANCREATIC | WT | MUTANT G12D | WT | MUTANT R273H |
| 14 | CTG-0381 | PANCREATIC | WT | MUTANT G12R | WT | WT |
| 15 | CTG-0306 | PANCREATIC | WT | MUTANT G12V | WT | WT |
| 16 | CTG-0289 | PANCREATIC | WT | MUTANT G12D | WT | WT |
| 17 | CTG-0292 | PANCREATIC | WT | WT | WT | MUTANT W91* |
| 18 | CTG-0283 | PANCREATIC | WT | MUTANT G12V | WT | MUTANT H179Q |
| 19 | CTG-0284 | PANCREATIC | WT | MUTANT G12D | WT | MUTANT C238Y |
| 20 | CTG-0301 | PANCREATIC | WT | WT | WT | ND |
| 21 | CTG-0295 | PANCREATIC | WT | MUTANT G12D | WT | WT |
| 22 | CTG-0309 | PANCREATIC | WT | MUTANT G12D | WT | MUTANT F109S |
| 23 | CTG-0287 | PANCREATIC | WT | MUTANT G12V | WT | MUTANT R282W |
| 24 | CTG-0411 | PANCREATIC | WT | MUTANT G12V | WT | WT |
| 25 | CTG-0780 | PANCREATIC | WT | MUTANT G12D | WT | MUTANT H178T |
|   |          |            |    |             |    | MUTANT R175G |
| 26 | CTG-0303 | PANCREATIC | WT | WT | WT | WT |
| 27 | CTG-0300 | PANCREATIC | WT | MUTANT G12V | WT | WT |

WT-WILD TYPE
ND-NOT DETERMINED

FIG. 8 Continued

TGF(β)-MIR200-MIG6 PATHWAY AND ITS USE IN THE TREATMENT OF CANCER AS AN INDICATOR OF RESISTANCE TO EGFR INHIBITORS

CROSS-REFERENCE TO RELATED APPLICATIONS

This application is a 35 U.S.C. § 371 U.S. national entry of International Application PCT/US2015/026986, having an international filing date of Apr. 22, 2015, which claims the benefit of U.S. Provisional Application No. 61/982,417, filed Apr. 22, 2014, the content of each of the aforementioned applications is herein incorporated by reference in their entirety.

BACKGROUND OF THE INVENTION

The sensitivity of some tumors to EGFR inhibitors can be explained by the presence of mutations in the EGFR tyrosine kinase domain. However, such mutations are rare in tumors other than non-small cell lung carcinoma (NSCLC).

The response to EGFR-targeted agents is inversely correlated with epithelial-mesenchymal transition (EMT) in multiple types of tumors without known EGFR mutations, including NSCLC, head and neck (H&N), bladder, colorectal, pancreas and breast carcinomas. Notably, epithelial tumor cells have been shown to be significantly more sensitive to EGFR inhibitors than tumor cells which have undergone an EMT-like transition and acquired mesenchymal characteristics. These data suggest that EMT is a common denominator of tumors that are resistant to EGFR inhibitors. However, the precise molecular mechanisms underlying this association have not been defined.

EMT is driven by a network of transcriptional repressors which include SNAIL1, SNAIL2 (SLUG), ZEB1 (zinc-finger E-box binding factor), ZEB2, and TWIST. TGFβ-activated SMAD3/4 stimulates the expression of SNAIL1 and TWIST1, which cooperate with SMAD proteins to repress the expression of epithelial genes such as CDH1 (which encodes E-cadherin). These transcriptional effects of TGFβ cooperate with TGFBR2-mediated phosphorylation of partitioning defective 6 (PAR6) to trigger EMT. Whereas TGFβ stimulates EMT, bone morphogenetic protein (BMP) signaling through SMAD1/4 induces expression of pro-epithelial microRNAs (miR200 and miR205) that oppose EMT. The miR200 family consists of five members localized on two genomic clusters that can be further divided into two subgroups according to their seed sequences—subgroup I: miR141 and miR-200a; subgroup II: miR200b, miR200c and miR-429 (16). During TGFβ-induced EMT, miR200 family and miR205, but not the other microRNAs, are greatly downregulated to facilitate this transition. Members of the miR200 family also influence sensitivity to EGFR inhibitors. miR200c may directly inhibit the expression of Mig6 (also known as RALT, ERRFI1 or Gene 33), a negative regulator of EGFR, which plays an important role in signal attenuation of the EGFR network by blocking the formation of the activating dimer interface through interaction with the kinase domains of EGFR and ERBB2.

Although EMT inversely correlates with the response of cancers to EGFR-targeted therapy, no specific EMT-associated biomarker of clinical benefit has been identified and patients with tumors expressing wild-type (wt) EGFR lack reliable predictive markers of their clinical response to EGFR TKIs. Therefore, there is a need to elucidate the mechanisms underlying the differential drug response of cancer cells with wt-EGFR in order to identify those patients who could respond and clinically benefit from TKIs, and to develop new therapeutic strategies to circumvent the de novo or acquired resistance of tumors to EGFR inhibitors.

SUMMARY OF THE INVENTION

In accordance with an embodiment, the present invention provides a method for identifying the susceptibility of a cancer cell or population of cells from a tumor to treatment with Epidermal Growth Factor Receptor (EGFR) tyrosine kinase inhibitors (TKI) comprising: a) obtaining a cancer cell or population of cells from a tumor; b) isolating a RNA sample from the cancer cell or population of cells; c) performing quantitative real-time PCR on the RNA from the sample of the cancer cell or population of cells using the PCR primers and probes specific for Mig6 mRNA, and for one or more microRNAs selected from the group consisting of: miR200a, miR200b, miR200c and miR205; d) determining the quantity of the Mig6 mRNA and the one or more microRNAs in the sample of the cancer cell or population of cells; e) comparing the quantity of the Mig6 mRNA to the quantity of the one or more microRNAs in the sample of the cancer cell or population of cells; f) identifying the cancer cell or population of cells from the tumor as being sensitive to treatment with EGFR TKI when the ratio of the quantity of the Mig6 mRNA to the quantity of the one or more microRNAs is less than or equal to about 0.05; and g) identifying the appropriate chemotherapeutic agent to treat the cancer cell or population of cells.

In accordance with a further embodiment, the present invention provides a method for monitoring the susceptibility of tumor in a subject to treatment with Epidermal Growth Factor Receptor (EGFR) tyrosine kinase inhibitors (TKI) comprising: a) isolating a RNA sample from a cancer cell or population of cells from the tumor of the subject; b) performing quantitative real-time PCR on the RNA from the sample of the cancer cell or population of cells using the PCR primers and probes specific for Mig6 mRNA, and for one or more microRNAs selected from the group consisting of: miR200a, miR200b, miR200c and miR205; c) determining the quantity of the Mig6 mRNA and the one or more microRNAs in the sample of the cancer cell or population of cells from the tumor; d) comparing the quantity of the Mig6 mRNA to the quantity of the one or more microRNAs in the sample of the cancer cell or population of cells; e) identifying the cancer cell or population of cells from the tumor as being sensitive to treatment with EGFR TKI when the ratio of the quantity of the Mig6 mRNA to the quantity of quantity of the one or more microRNAs is less than or equal to about 0.05; and f) identifying whether a change to the chemotherapeutic regimen to treat the subject is needed if the ratio of the quantity of the Mig6 mRNA to the quantity of the one or more microRNAs indicates resistance to treatment.

In accordance with an embodiment, the present invention provides a method for inducing susceptibility of a cell or population of cells in a tumor from a subject comprising contacting a cell or population of cells of the tumor with at least one biologically active agent which blocks the effect of TGFβ on the cell or population of cells in the tumor.

BRIEF DESCRIPTION OF THE DRAWINGS

FIGS. 2A-2F depict that increased production of TGFβ induces an EMT-associated kinase switch which promotes erlotinib-resistance of tumor cells. A. Protein lysates were extracted from indicated cell lines Immunoblot analysis was performed with antibodies against E-cadherin, vimentin and β-actin. B. Tumor cell supernatants of 25 cancer cell lines shown in A were collected and differential levels of TGFβ production were analyzed by ELISA. C. Erlotinib sensitive lung cancer cell line H358 was treated with TGFβ1/TGFβ3 (4 ng/ml) or control vehicle for 21 days. Cells were collected at different time points and Immunoblot analysis was performed with indicated antibodies. D. Parental and TGFβ-induced H358 cells were treated with erlotinib for 72 hours at indicated time points and cell viability was assayed. Values were set at 100% for untreated controls. E. Cells treated with TGFβ1/TGFβ3 or control vehicle for 21 days were exposed to LY294002, U0126, or erlotinib for 24 hours Immunoblot analysis was performed with antibodies against Mig6 and β-actin. F. Protein lysates were extracted from H358 cells treated with TGFβ1 or control vehicle for 21 days and immunoblot analysis was performed with antibodies against indicated RTKs. β-actin was used as a loading control.

FIGS. 3A-3C show that TGFβ-induced EMT and erlotinib resistance is associated with decreased levels of the miR200 family and increased Mig6 expression. A. Erlotinib sensitive cell lines H358, H292 and SCC-S were exposure to TGFβ for 21 days. RNA was extracted and expression levels of miR200a, miR200b, miR200c and miR205 were quantified by real-time PCR. B. RNA was extracted from four sensitive/resistant cancer cell lines pairs. Levels of miR200a, miR200b, miR200c and miR205 were measured and relative expression is presented as average fold change of each miRNA in erlotinib-sensitive cell lines relatively to that in resistant cells, which was given a value 1. C. qRT-PCR analysis of miR200a, miR200b, miR200c and miR205 in a panel of 25 human cancer cell lines with known erlotinib sensitivity. Relative quantification of miRNA expression was performed by using RNU6b as an internal control. The results are presented as expression average of each miRNA in erlotinib-sensitive cell lines relatively to that in erlotinib-resistant cells.

FIGS. 5A-5C show that an elevated ratio of Mig6 (mRNA)/miR200 expression is associated with erlotinib resistance in cancer cell lines of different tissue origins. A. Levels of Mig6 protein (gray bars) or mRNA transcript (white bars) were measured in the panel of 25 human cancer cell lines and plotted on a single graph. B. Scatter plot showing the ratio between Mig6 mRNA and each one of the tested microRNAs (log2 scale) plotted against the $IC_{50}$ of the corresponding cell line. C. The exposure density of both EGFR and Mig6 blotted on the same membrane were quantified by densitometry and the values of Mig6/EGFR (log2 scale) were plotted against $IC_{50}$.

FIG. 8 depicts Table 1, identifying tumor characteristics, including KRAS, NRAS and p53 mutation status.

DETAILED DESCRIPTION OF THE INVENTION

Figure 1A:
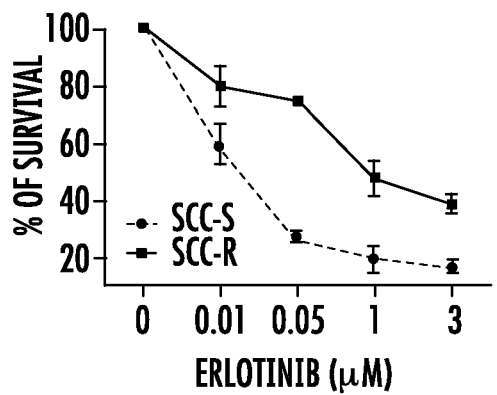
FIGS. 1A-1C show that erlotinib-resistant phenotype is associated with a kinase switch that enables EGFR-independent activation of AKT. A. Two pairs (sensitive/resistant) of lung (H358/H1703 and Calu3/Calu6) and two pairs of H&N (SCC-S/SCC-R and JHU011/JHU028) cancer cell lines were treated with the indicated concentrations of erlotinib and cell viability was assayed. Values were set at 100% for untreated controls. B. Cells were subjected to immunoblot analysis with antibodies specific for phosphorylated and total EGFR, HER2, HER3, AKT and total Mig6. β-actin was used a control. C. Western blot analysis demonstrates expression and activation levels of the indicated RTKs in four pairs of erlotinib resistant/sensitive cell lines.
Figure 1A:
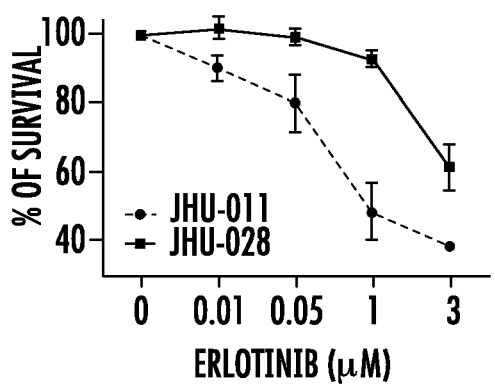
Figure 1A:
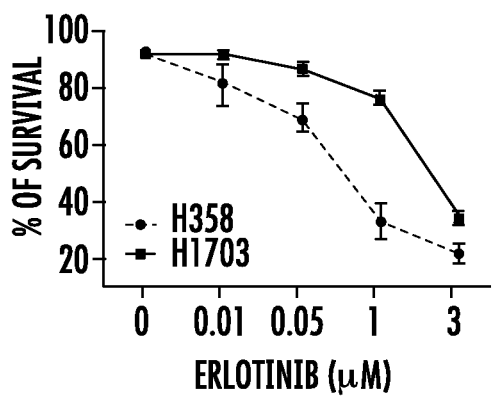
Figure 1A:
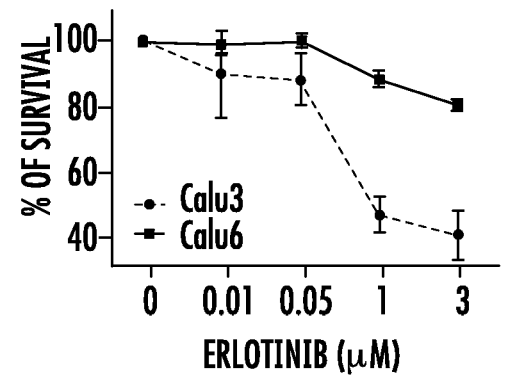

In accordance with some embodiments, the present inventors found that in response to tumor cell-autonomous expression of TGFβ, erlotinib-sensitive tumor cells undergo EMT-associated suppression of the miR200 family and subsequent upregulation of Mig6 expression. The inventors show that the Mig6-mediated reduction of EGFR occurs concomitantly with a TGFβ-induced EMT-associated kinase switch of tumor cells to an AKT-activated state, thereby leading to an EGFR-independent phenotype that is refractory to EGFR TKI. In a panel of 25 cancer cell lines of different tissue origins, it was found that the ratio of the expression levels of Mig6 and miR200c is highly correlated with EMT and resistance to erlotinib. Moreover, analyses of primary tumor xenografts of patient-derived lung and pancreatic cancers carrying wt-EGFR showed that the tumor Mig6 (mRNA)/miR200 ratio is inversely correlated with response to erlotinib in vivo. The present findings demonstrate that the TGFβ-miR200-Mig6 network orchestrates the EMT-associated kinase switch that induces resistance to EGFR inhibitors, and identify the ratio of Mig6 to miR200 as a promising predictive biomarker of the response of tumors to EGFR TKIs.

Thus, in accordance with an embodiment, the present invention provides a method for identifying the susceptibility of a cancer cell or population of cells from a tumor to treatment with Epidermal Growth Factor Receptor (EGFR) tyrosine kinase inhibitors (TKI) comprising: a) obtaining a cancer cell or population of cells from a tumor; b) isolating a RNA sample from the cancer cell or population of cells; c) performing quantitative real-time PCR on the RNA from the sample of the cancer cell or population of cells using the PCR primers and probes specific for Mig6 mRNA, and for one or more microRNAs selected from the group consisting of: miR200a, miR200b, miR200c and miR205; d) determining the quantity of the Mig6 mRNA and the one or more microRNAs in the sample of the cancer cell or population of cells; e) comparing the quantity of the Mig6 mRNA to the quantity of the one or more microRNAs in the sample of the cancer cell or population of cells; f) identifying the cancer cell or population of cells from the tumor as being sensitive to treatment with EGFR TKI when the ratio of the quantity of the Mig6 mRNA to the quantity of quantity of the one or more microRNAs is less than or equal to about 0.05; and g) identifying the appropriate chemotherapeutic agent to treat the cancer cell or population of cells.

In accordance with another embodiment, the present invention provides a method for identifying the susceptibility of a cancer cell or population of cells from a tumor to treatment with Epidermal Growth Factor Receptor (EGFR) tyrosine kinase inhibitors (TKI) comprising: a) isolating a RNA sample from a cancer cell or population of cells from a tumor; b) performing quantitative real-time PCR on the RNA from the sample of the cancer cell or population of cells using the PCR primers and probes specific for Mig6 mRNA, and for one or more microRNAs selected from the group consisting of: miR200a, miR200b, miR200c and miR205; c) determining the quantity of the Mig6 mRNA and the one or more microRNAs in the sample of the cancer cell or population of cells; d) comparing the quantity of the Mig6 mRNA to the quantity of the one or more microRNAs in the sample of the cancer cell or population of cells; e) identifying the cancer cell or population of cells from the tumor as being sensitive to treatment with EGFR TKI when the ratio of the quantity of the Mig6 mRNA to the quantity of quantity of the one or more microRNAs is less than or equal to about 0.05; and f) identifying the appropriate chemotherapeutic agent to treat the cancer cell or population of cells from the tumor.

As used herein, the term "Epidermal Growth Factor Receptor (EGFR) tyrosine kinase inhibitors (TKI)" means a class of small molecules which compete with the ATP binding site of the catalytic domain of several oncogenic tyrosine kinases. They are generally orally active, small molecules that have a favorable safety profile and can be easily combined with other forms of chemotherapy or radiation therapy. Several TKIs have been found to have effective antitumor activity and have been approved or are in clinical trials. Examples of such inhibitors include, but are not limited to. imatinib mesylate (STI571; Gleevec), gefitinib (Iressa), erlotinib (OSI-1774; Tarceva), lapatinib (GW-572016), canertinib (CI-1033), semaxinib (SU5416), vatalanib (PTK787/ZK222584), sorafenib (BAY 43-9006), sutent (SU11248), and leflunomide (SU101).

Isolation of RNA from biological samples is routine in the art, and the methods are not limited to any particular isolation technique. In general, RNA was extracted using Trizol (Invitrogen, Carlsbad, Calif.) followed by RNeasy kit cleanup (Qiagen, Valencia, Calif.). RNA was reverse transcribed to cDNA using Superscript III (Invitrogen) which was then used as a template for real-time PCR. Gene products were amplified using iTaq SYBR green Supermix with Rox dye. For quantitative real-time PCR for microRNAs, RNA was extracted using the mirVana™ Kit (Ambion, Austin, Tex.). Total RNA from fresh frozen tumors was isolated using the Trizol reagent (Invitrogen, Carlsbad, Calif.). Specific quantitative real-time PCR was carried out using TaqMan MicroRNA Assays for miR200a, miR200b, miR200c, miR205 and control RNU6b (Applied Biosystems, Foster City, Calif.) on a 7900HT detector (Applied Biosystems, Foster City, Calif.).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In an embodiment, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids used as primers in embodiments of the present invention can be constructed based on chemical synthesis and/or enzymatic ligation reactions using procedures known in the art. See, for example, Sambrook et al. (eds.), *Molecular Cloning, A Laboratory Manual*, 3$^{rd}$ Edition, Cold Spring Harbor Laboratory Press, New York (2001) and Ausubel et al., *Current Protocols in Molecular Biology*, Greene Publishing Associates and John Wiley & Sons, NY (1994). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleotide sequences used herein are those which hybridize under stringent conditions preferably hybridizing under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C.

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

A method of identifying a nucleic acid associated with a disease or a pathological condition is also provided. The method comprises measuring a level of the nucleic acid in a sample that is different than the level of a control. In accordance with an embodiment, the nucleic acid is a miRNA and the detection may be performed by contacting the sample with a probe or biochip described herein and detecting the amount of hybridization. PCR may be used to amplify nucleic acids in the sample, which may provide higher sensitivity.

The term "isolated and purified" as used herein means a RNA that is essentially free of association with other proteins or polypeptides, or nucleic acids e.g., as a naturally occurring RNA that has been separated from cellular and other contaminants by the use of probes or other methods or as a purification product of a recombinant host cell culture.

The miRNA sample can be amplified and labeled as is appropriate or desired. If amplification is desired, methods known to those skilled in the art can be applied. The miRNA samples can be labeled using various methods known to those skilled in the art. In accordance with an embodiment, the miRNA samples are labeled with digoxigenin using a Digoxigenin (DIG) Nucleotide Tailing Kit (Roche Diagnostics Corporation, Indianapolis, Ind.) in a GeneAmp® PCR System 9700 (Applied Biosystems, Foster City, Calif.).

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In accordance with one or more embodiments of the present invention, it will be understood that the diagnosis of whether the cancer cell or population of cells from a tumor is susceptible to TKIs which may be made, using the methods provided herein, is not necessarily limited. For purposes herein, the cancer can be any cancer. As used herein, the term "cancer" is meant any malignant growth or tumor caused by abnormal and uncontrolled cell division that may spread to other parts of the body through the lymphatic system or the blood stream.

In an embodiment, the term "administering" means that the compounds of the present invention are introduced into a subject, preferably a subject receiving treatment for a proliferative disease, and the compounds are allowed to come in contact with the one or more disease related cells or population of cells in vivo.

The cancer can be a metastatic cancer or a non-metastatic (e.g., localized) cancer. As used herein, the term "metastatic cancer" refers to a cancer in which cells of the cancer have metastasized, e.g., the cancer is characterized by metastasis of a cancer cells. The metastasis can be regional metastasis or distant metastasis, as described herein.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of diagnosis, staging, screening, or other patient management, including treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se, as well as pharmaceutically acceptable, pharmacologically active salts, esters, amides, prodrugs, metabolites, analogs etc.

In accordance with another embodiment of the present invention, it will be understood that the term "biological sample" or "biological fluid" includes, but is not limited to, any quantity of a substance from a living or formerly living patient or mammal. Such substances include, but are not limited to, tumor cells, blood, serum, plasma, urine, cells, organs, tissues, bone, bone marrow, lymph, lymph nodes, synovial tissue, chondrocytes, synovial macrophages, endothelial cells, and skin. In a preferred embodiment, the sample is from a tumor cell.

It is also contemplated that in an embodiment of the present invention, the methods of treatment disclosed herein are useful against many mammalian tumors, including, for example, breast cancer, prostate cancer, pancreatic cancer, colon cancer, hepatoma, glioblastoma, ovarian cancer, and others.

It will be understood by those of ordinary skill in the art that the term "tumor" as used herein means a neoplastic growth which may, or may not be malignant. Additionally, the compositions and methods provided herein are not only useful in the treatment of tumors, but in their micrometastses and their macrometastses. Typically, micrometastasis is a form of metastasis (the spread of a cancer from its original location to other sites in the body) in which the newly formed tumors are identified only by histologic examination; micrometastases are detectable by neither physical exam nor imaging techniques. In contrast, macrometastases are usually large secondary tumors.

In accordance with some embodiments, the present invention provides method of identifying whether a cancer cell or population of cells is susceptible to treatment with TKIs. In particular, the measurement of the quantity of Mig6 mRNA and quantity of miR200 family microRNA is measured using RT-PCR and Quantitative real-time PCR respectively. The inventive methods are used to create a ratio of the quantity of Mig6 mRNA vs. the quantity of miR200 family microRNA. It was found that there was an inverse correlation between ratio of the quantity of Mig6 mRNA vs. the quantity of miR200 family microRNA and tumor susceptibility to TKIs, i.e., a low ratio (>0.05) indicates TKI sensitivity, and a high ratio (<0.1) indicates TKI resistance.

Thus, one or ordinary skill in the art would understand that these findings are valuable in diagnosing and indicating a particular treatment regimen for a subject with a tumor, e.g., a tumor sample indicating TKI sensitivity would result in a diagnosis of the subject as having a TKI sensitive tumor and appropriate treatment regimens including TKIs would be prescribed and/or administered. Conversely, a tumor sample indicating TKI resistance would result in a diagnosis of the subject as having a TKI resistant tumor and appropriate treatment regimens either omitting TKIs or TKIs with other chemotherapeutic agents known in the art would be prescribed and/or administered.

In another embodiment, the inventive methods can also be used during treatment of a subject as a means of monitoring the cancer in the patient for acquisition of an erlotinib-resistant EMT phenotype tumor, for example, measuring the ratio of the quantity of Mig6 mRNA vs. the quantity of miR200 family microRNA, prior to chemotherapy, and during treatment can be used to determine whether the tumor of the subject is becoming resistant to TKI therapy.

Therefore, in accordance with a further embodiment, the present invention provides a method for monitoring the susceptibility of tumor in a subject to treatment with Epidermal Growth Factor Receptor (EGFR) tyrosine kinase inhibitors (TKI) comprising: a) isolating a RNA sample from a cancer cell or population of cells from the tumor of the subject; b) performing quantitative real-time PCR on the RNA from the sample of the cancer cell or population of cells from the tumor using the PCR primers and probes specific for Mig6 mRNA, and for one or more microRNAs selected from the group consisting of: miR200a, miR200b, miR200c and miR205; c) determining the quantity of the Mig6 mRNA and the one or more microRNAs in the sample of the cancer cell or population of cells; d) comparing the quantity of the Mig6 mRNA to the quantity of the one or more microRNAs in the sample of the cancer cell or population of cells from the tumor; e) identifying the cancer cell or population of cells as being sensitive to treatment with EGFR TKI when the ratio of the quantity of the Mig6 mRNA to the quantity of the one or more microRNAs is less than or equal to about 0.05; and g) identifying whether a change to the chemotherapeutic regimen to treat the subject is needed if the ratio of the quantity of the Mig6 mRNA to the quantity of quantity of the one or more microRNAs indicates loss of sensitivity to treatment.

In accordance with a further embodiment, the present invention provides a method for the in vitro/ex vivo monitoring the susceptibility of a tumor in a subject to treatment with Epidermal Growth Factor Receptor (EGFR) tyrosine kinase inhibitors (TKI) comprising: a) performing quantitative real-time PCR on the RNA on a sample of the cancer cell or population of cells from the tumor using the PCR primers and probes specific for Mig6 mRNA, and for one or more microRNAs selected from the group consisting of: miR200a, miR200b, miR200c and miR205; b) determining the quantity of the Mig6 mRNA and the one or more microRNAs in the sample of the cancer cell or population of cells; c) comparing the quantity of the Mig6 mRNA to the quantity of the one or more microRNAs in the sample of the cancer cell or population of cells; d) identifying the cancer cell or population of cells from the tumor as being sensitive to treatment with EGFR TKI when the ratio of the quantity of the Mig6 mRNA to the quantity of quantity of the one or more microRNAs is less than or equal to about 0.05; e) identifying whether a change to the chemotherapeutic regimen to treat the subject is needed if the ratio of the quantity of the Mig6 mRNA to the quantity of quantity of the one or more microRNAs indicates loss of sensitivity to treatment.

Furthermore, in an alternative embodiment, the inventive methods can be used to monitor TKI resistance in a tumor after treating the tumor of the subject with TGFβ inhibiting compounds. The inventors have shown that inhibition of TGFβ in a TKI resistant tumor can convert the tumor from a resistant phenotype to a more sensitive phenotype, where it could be treated with TKIs.

Examples of such TGFβ inhibitors are known in the art, including, for example, SB-431542, A-83-01, D-4476, LY-364947, GW-788388, SB-505124, or TGFβ RII/Fc.

Thus, in accordance with an embodiment, the present invention provides a method for inducing susceptibility of a cell or population of cells in a tumor from a subject comprising contacting the cell or population of cells of the tumor with at least one biologically active agent which blocks the effect of TGFβ on the cell or population of cells in the tumor.

EXAMPLES

Compounds and reagents. Erlotinib was purchased from Johns Hopkins Hospital Pharmacy. LY294002 and U0126 were obtained from Cell Signaling (Beverly, Mass.). TGFβ and TGFβ RII/Fc were purchased from R&D Systems (Minneapolis, Minn.). All other chemicals were purchased from Sigma (St. Louis, Mo.). All reagents were dissolved according to the manufacturer's recommendations.

Cell lines. Human NSCLC cell lines (H226, H292, H358, H1838, A549, Calu6, H460, H1703, H1915, H1299, Calu3, H1437, and H23), human bladder cancer cell lines (5637, SCaBER, UMUC-3, T24, HT-1376, BFTC-905 and J82) and human HNSCC cell line FaDu were obtained from American Type Culture Collection (ATCC).

Establishment of acquired resistance to erlotinib. Drug resistant cell lines were generated via a process of slowly escalating exposure to erlotinib, as reported previously (PloS one.8:e68966). SCC-S is used to designate the parental UM-SCC1 cells exposed to DMSO, and SCC-R refers to the erlotinib resistant clone.

Antibodies and immunoblot analysis. Pelleted cells were lysed on ice by adding RIPA lysis buffer (Thermo Scientific, Rockford, Ill.) supplemented with protease and phosphatase inhibitors (Roche, Basel, Switzerland). Protein concentrations were determined by the BCA method and lysates diluted in SDS sample buffer (Bio-Rad, Hercules, Calif.) prior to SDS-PAGE. Anti-Mig6 antibody was a gift from Dr. Ferby (Nature medicine. 2006; 12:568-73). β-actin was obtained from Abcam (Cambridge, Mass.). All other antibodies were obtained from Cell Signaling (Beverly, Mass.). Secondary horseradish peroxidase (HRP)-conjugated antibodies were from KPL (Gaithersburg, Md.) and signals developed using West-Pico chemiluminescence substrate (Thermo Scientific). ImageJ (ver 1.46) software was used to quantify immunoblot signals on exposed films.

Reverse transcription and real-time PCR. RNA was extracted using Trizol (Invitrogen, Carlsbad, Calif.) followed by RNeasy kit cleanup (Qiagen, Valencia, Calif.). RNA was reverse transcribed to cDNA using Superscript III (Invitrogen) which was then used as a template for real-time PCR. Gene products were amplified using iTaq SYBR green Supermix with Rox dye (Bio-Rad Laboratories, Hercules, Calif.). All reactions were performed in triplicate and relative quantity was calculated after normalizing to GAPDH expression.

Quantitative real-time PCR for miRNA. RNA from cultured cells was extracted using the mirVana™ Kit (Ambion, Austin, Tex.). Total RNA from fresh frozen tumors was isolated using the Trizol reagent (Invitrogen, Carlsbad, Calif.). Specific quantitative real-time PCR was carried out using TaqMan MicroRNA Assays for miR200a, miR200b, miR200c, miR205 and control RNU6b (Applied Biosystems, Foster City, Calif.) on a 7900HT detector (Applied Biosystems, Foster City, Calif.).

Cell viability assay. Relative cell viability was determined using an Alamar Blue assay as outlined by the manufacturer (AbDSerotec, Raleigh, N.C.). New media containing 1/10 volume of Alamar Blue reagent was added to the wells and cells were incubated at 37° C. for 1 hour. Fluorescence (545 nm excitation, 590 nm emission wavelengths) was measured using a SpectraMax Plus384 fluorometer (Sunnyvale, Calif.). Cell viability was calculated relative to an untreated culture of cells incubated in parallel.

Measurement of TGFβ in tumor cell supernatants. $1\times10^6$ cells were plated in media containing 0.1% FBS. Tumor cell supernatants were evaluated by ELISA (R&D Systems) to determine the amount of TGFβ expressed by $1\times10^6$ cells per 24 hours.

Xenograft generation. The xenografts were generated and erlotinib treatment was performed as published previously (Cancer research. 2008;68:2841-9; J Proteome Res., 2008; 7:4651-8). Relative tumor growth inhibition (TGI) in response to Erlotinib (35 mg/kg) was calculated as the relative tumor growth of treated mice divided by relative tumor growth of control mice (T/C). The animals were maintained in accordance to guidelines of the American Association of Laboratory Animal Care and the research protocol was approved by the Johns Hopkins University Animal Use and Care Committee.

Statistical analysis. Student t-tests were used for statistical analysis between two groups. The significance level was defined as 0.05. All statistical analyses were performed using SPSS. $IC_{50}$ was generated using GraphPad Prism software (La Jolla, Calif.).

Example 1

Figure 1B:
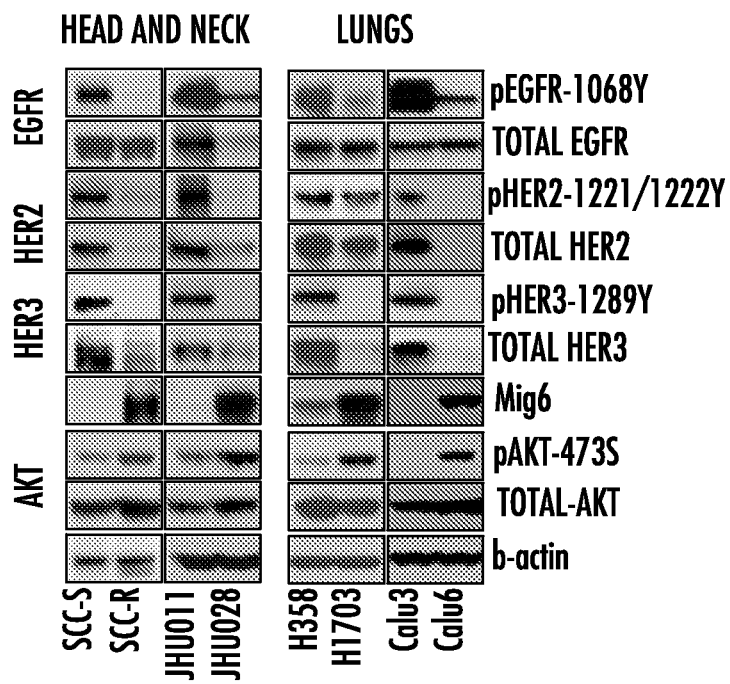
Figure 1C:
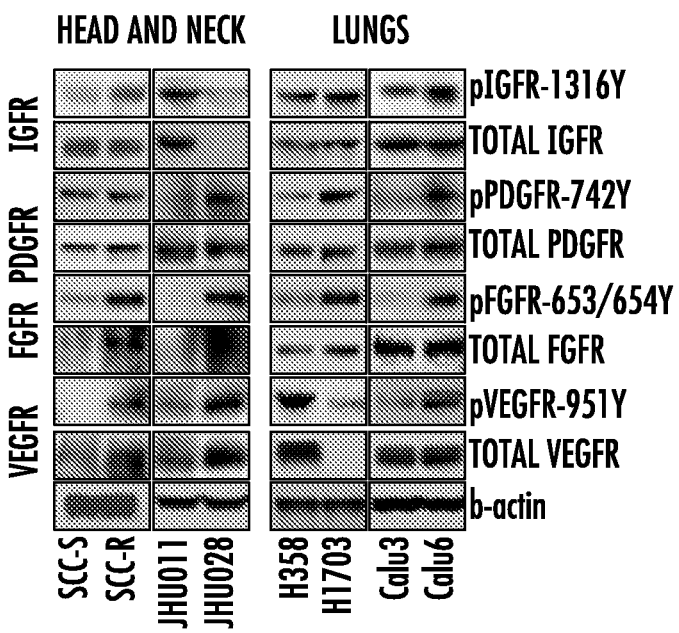

The Erlotinib-resistant tumor phenotype is associated with a kinase switch that enables EGFR-independent activation of AKT. To identify the molecular mechanisms underlying the resistance of tumor cells to EGFR TKI, we examined tumor cell expression and activity of EGFR and alternative receptor tyrosine kinases (RTKs) that lead to EGFR-independent AKT activation. We evaluated pairs of cancer cell lines with wt-EGFR that were either sensitive or resistant to the EGFR TKI, erlotinib; lung carcinoma (H358/ H1703 and Calu3/Calu6) and H&N cancer (SCC-S/SCC-R and JHU011/JHU028). Erlotinib-resistant (SCC-R) and erlotinib-sensitive (SCC-S) isogenic cell lines were generated by chronic exposure of human H&N squamous cell carcinoma UM-SCC1 cells to either erlotinib or DMSO (vehicle control). The other three pairs of cell lines (JHU011/JHU028, H358/H1703 and Calu3/Calu6) are intrinsically erlotinib-sensitive or erlotinib-resistant. For every sensitive/resistant cell line pair tested, the $IC_{50}$ of the resistant cells was at least 10 times higher than that of their sensitive counterparts (FIG. 1A). Comparison of the expression and activity of EGFR family members in resistant and sensitive cell lines revealed that the levels of phosphorylated EGFR, HER2 and HER3 were markedly decreased in resistant cells (FIG. 1B). In resistant cells, low activity of EGFR family kinases was associated with a significantly higher expression of the endogenous EGFR family negative regulator, Mig6. Consistent with the observed upregulation of Mig6 expression by PI3K-dependent pathways (Oncogene. 2002; 21:6530-9), the resistant cell lines exhibited higher AKT phosphorylation levels compared to their sensitive counterparts (FIG. 1B). In accordance with their increased AKT phosphorylation despite low activity of the EGFR family members, erlotinib-resistant cells exhibited a switch from EGFR to activation of an alternative tumor cell-specific RTKs (PDGFR, FGFR, VEGFR, and/or IGFR) (FIG. 1C).

Example 2

Figure 2A:
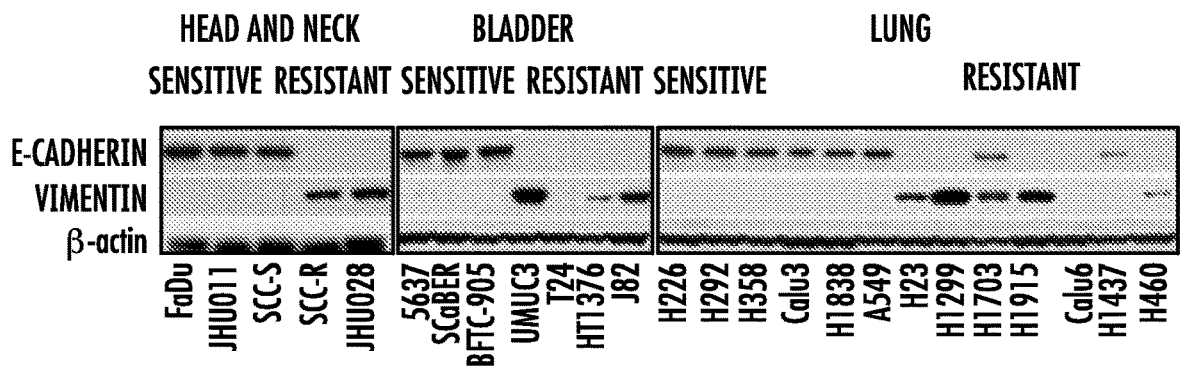
Figure 2B:
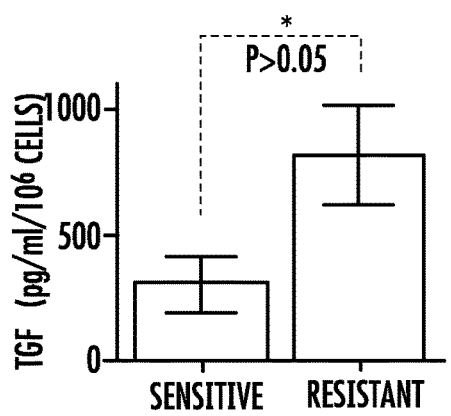
Figure 2C:
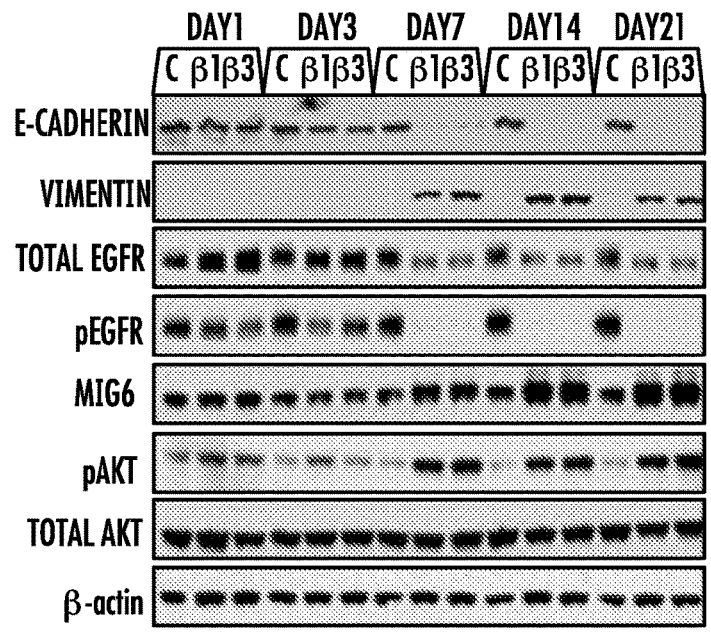

Increased production of TGFβ induces an EMT-associated kinase switch that promotes erlotinib-resistance of tumor cells. The non-receptor focal adhesion kinase (FAK) plays an important role in TGFβ-induced EMT progression and up-regulation of mesenchymal markers. We tested FAK phosphorylation and total expression level in our four pairs of erlotinib resistant and sensitive cell lines and found that FAK activity is significantly higher in erlotinib-resistant cells from lung and H&N origin (data not shown). To evaluate whether resistance to erlotinib is associated with features of EMT, we tested levels of E-cadherin and vimentin in the panel of 25 erlotinib-sensitive or erlotinib-resistant cell lines with wt-EGFR from lung, H&N and bladder cancer origin. While erlotinib-sensitive cells displayed characteristics of typical epithelial cells, including expression of E-cadherin and absence of vimentin, the majority of resistant cells displayed a mesenchymal phenotype manifested by loss of E-cadherin and acquisition of vimentin (FIG. 2A). To determine whether erlotinib sensitivity correlates with levels of tumor cell expression of TGFβ, we measured the amount of TGFβ produced in cell supernatants of each of the 25 tumor cell lines. Erlotinib-resistant, mesenchymal-like tumor cell lines produced higher levels of TGFβ compared to the erlotinib-sensitive, epithelial-like tumor cells (FIG. 2B). To examine whether TGFβ induces the EMT-associated kinase switch responsible for resistance to erlotinib, erlotinib-sensitive epithelial cell lines were exposed to TGF-β1 or TGF-β3. These cell lines included one H&N (SCC-S) and two lung (H358 and H292) cancer cell lines. Serial examination of EMT markers (loss of E-cadherin and upregulation of vimentin) in a time course (1-21 days) showed that TGF-β treatment resulted in complete EMT by day 14 (FIG. 2C and not shown). Strikingly, both total EGFR and phospho-EGFR were reduced with this transition and was accompanied by elevated expression of Mig6 in cells with a mesenchymal phenotype (FIG. 2C). Concomitant with these molecular alterations, the mesenchymal-like cells acquired a relative resistance to erlotinib (FIG. 2D). The acquisition of an erlotinib-resistant EMT phenotype in response to TGFβ was associated with a significant increase in AKT activity (FIG. 2C). To confirm the causal role of AKT in upregulating Mig6 in tumor cells that have acquired resistance to erlotinib, we treated H358, H358/TGFβ1-day 21, and H358/TGFβ3-day 21 cells with LY294002 (PI3K inhibitor), U0126 (MEK inhibitor) or erlotinib (FIG. 2E). Whereas all three inhibitors reduced basal expression of Mig6 in H358 cells, only LY294002 resulted in significant inhibition of Mig6 in the erlotinib-resistant H358/TGFβ1-day 21 and H358/TGFβ3-day 21 cells. These data indicate that basal EGFR activity induces an autoregulatory expression of Mig6 in epithelial cells, and that TGFβ-induced activation of AKT coopts this activity in mesenchymal cells (FIG. 2E). Together with the data shown in FIG. 1C, these data suggested that Mig6 elevation in EMT cells is due to activation of AKT by EGFR-independent tyrosine kinases. To test whether TGFβ can promote this kinase switch, levels of phospho IGFR, PDGFR, FGFR and FAK kinases were assessed in response to treatment of erlotinib-sensitive cells (H358, H292 and SCC-S) with TGFβ1 for 21 days. These kinases showed significantly greater activity in TGFβ1-treated cells when compared to the untreated counterparts (FIG. 2F and not shown). These data indicate that TGFβ-mediated activation of AKT via alternative kinases may substitute for the loss of EGFR activity in a cell-specific manner and contribute to the acquisition of an erlotinib-resistant phenotype.

Example 3

Figure 3C:
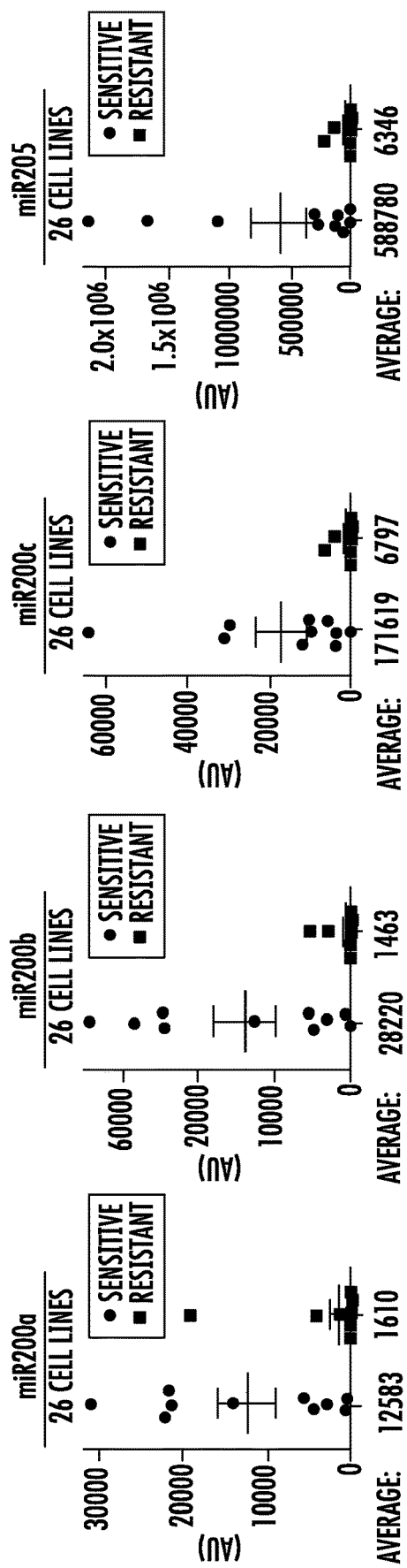

TGFβ-induced EMT and erlotinib resistance is associated with decreased levels of the miR200 family and increased Mig6 expression. Since the miR-200 family of microRNAs is downregulated to facilitate EMT, we used RT-PCR to assess the level of expression of miR200 in 3 sensitive cell lines (SCC-S, H358 and H292) in response to exposure to TGF3 for 21 days. In all tested cell lines, expression of the miR200 family members (200a, 200b, 200c and 205) was significantly reduced upon TGFβ treatment (FIG. 3A). Consistent with the observed ability of miR200c to directly inhibit expression of Mig6, the loss of miR200 family in response to TGFβ was attended with elevation in Mig6 expression during EMT-associated resistance to erlotinib (FIG. 2C and nor shown). We next examined changes in miR200 levels in erlotinib-sensitive (SCC-S) and erlotinib-resistant (SCC-R) isogenic H&N cell lines. We found that parental erlotinib-sensitive SCC-S cells displayed significantly higher levels of miR200 family members than the resistant, mesenchymal like, SCC-R cells (FIG. 3B). The same pattern was observed in the other three intrinsically sensitive/resistant cell lines pairs (JHU011/JHU028, H358/H1703 and Calu3/Calu6). Finally, examination of the 25 H&N, bladder, and lung cancer cell lines used in this study demonstrated a clear inverse correlation of miR200 levels and erlotinib sensitivity (FIG. 3C). Notably, the levels of miR200 family members were also inversely correlated with the expression of Mig6. While erlotinib-sensitive cells demonstrated a high level of miR200 and a low level of Mig6, most of the erlotinib-resistant cells showed decreased levels of miR200 microRNAs and elevated Mig6 expression (FIG. 3C and not shown). Taken together, these data indicate that TGFβ-induced repression of miR200 family unleashes the expression of Mig6 in tumor cells during their EMT-associated conversion to an erlotinib-resistant phenotype.

Example 4

Figure 4A:
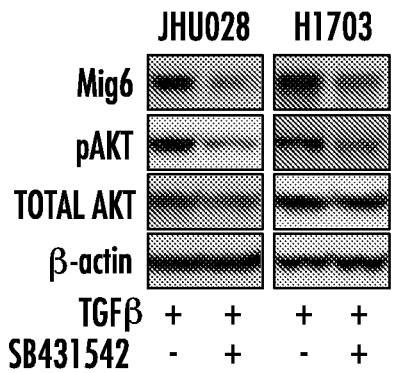
FIGS. 4A-4C depict that inhibition of TGFβ signaling results in upregulation of miR200c and miR205, decrease in Mig6 levels, and increased erlotinib sensitivity. Two erlotinib-resistant cell lines (JHU028 and H1703) were treated with TGFβ (2 ng/ml) alone or in combination with SB-431542 (10 μM) for 7 days. A. Cell lysates were collected and subjected to immunoblot analysis with indicated antibodies. B. Levels of miR200c and miR205 were measured and relative expression is presented as ΔΔCt. C. Cells were incubated with TGFβ (2 ng/ml) alone or in combination with either SB-431542 (10 μM) or TGFβ RII/Fc (20 ng/ml) for 7 days and then were treated with 1 μM of erlotinib for an additional 72 hours. Cell viability was assayed and values were set at 100% for untreated controls.
Figure 4B:
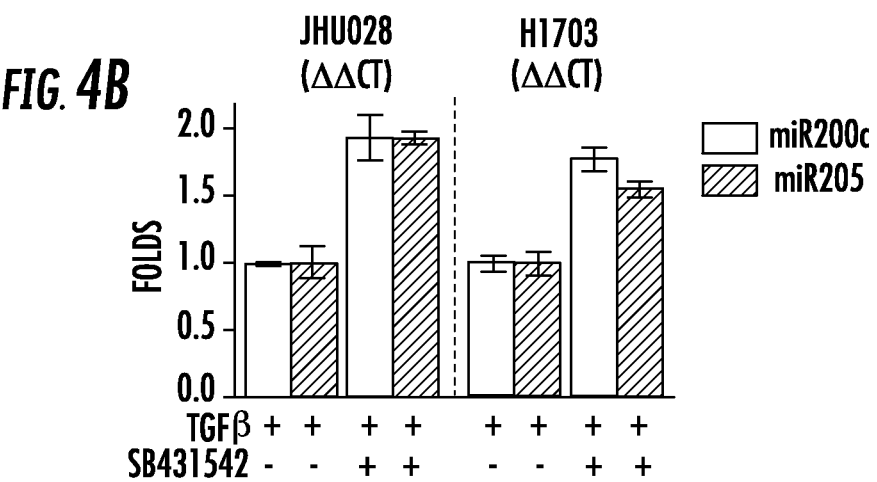
Figure 4C:
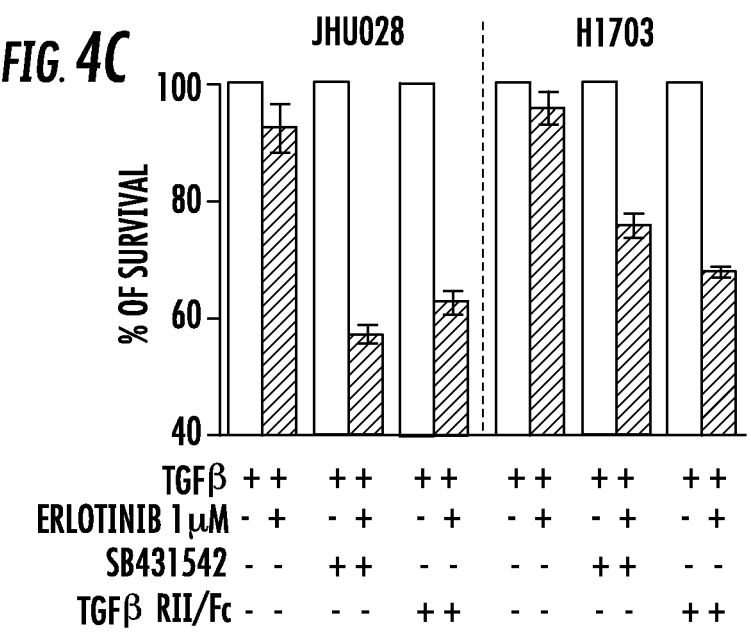

Inhibition of TGFβ signaling results in upregulation of miR200c and miR205, decrease in Mig6 levels, and increased erlotinib sensitivity. Autocrine or paracrine TGF3 signaling is required for the maintenance of the mesenchymal state. Blockage of this signaling can inhibit or reverse EMT by upregulating miR200 and subsequently downregulating ZEB1/2 (28-31). As a corollary to this observation, over-expression of miR-200c restores the sensitivity of resistant NSCLC cells to the anti-EGFR antibody cetuximab. To determine whether inhibition of TGFβ can restore miR200 expression and reverse the erlotinib-resistant phenotype, we blocked TGFβ signaling in two erlotinib-resistant cell lines of lung (H1703) and H&N (JHU028) origin with SB-431542, a potent inhibitor of the activin receptor-like kinase (ALK) receptors family. Tumor cells were cultured with TGFβ alone or in combination with TGFβ-inhibitor for 7 days, and then treated with 1 μM erlotinib for an additional 72 hours. In both cell lines, exposure to TGFβ-inhibitor resulted in a significant increase in miR200c and miR205 levels, and concurrent downregulation of AKT phosphorylation and Mig6 expression (FIGS. 4A,B). Treatment with SB-431542 increased the sensitivity of tumor cells to erlotinib (FIG. 4C). Likewise, cells incubated with TGFβ RII/Fc (recombinant TGFβ receptor II, which binds to and inhibits TGF-β1, TGF-β3, and TGF-β5), displayed a similar increase in erlotinib sensitivity (FIG. 4C).

Example 5

Elevated ratio of Mig6(mRNA)/miR200 expression is associated with erlotinib resistance in cancer cell lines of different tissue origins. We observed a strong correlation between Mig6 mRNA and protein levels in 25 tumor cell lines (FIG. 5A). Akin to the Mig6 protein, Mig6 mRNA expression was considerably lower in erlotinib-sensitive cell lines. Next we tested whether the ratio between Mig6 mRNA and miR200 levels is a reliable predictor of tumor cells response to erlotinib. We found that across the panel of 25 cancer cell lines, the ratio of Mig6 mRNA to each one of the miR200 family members tested appeared to be a reliable predictor of tumor cell responsiveness to erlotinib (FIG. 5B). Interestingly, the ability of Mig6(mRNA)/miR200 ratio to predict erlotinib sensitivity in cancer cell lines was equal or better than the predictive value of the Mig6/EGFR protein expression ratio (FIG. 5C).

Example 6

Figure 6A:
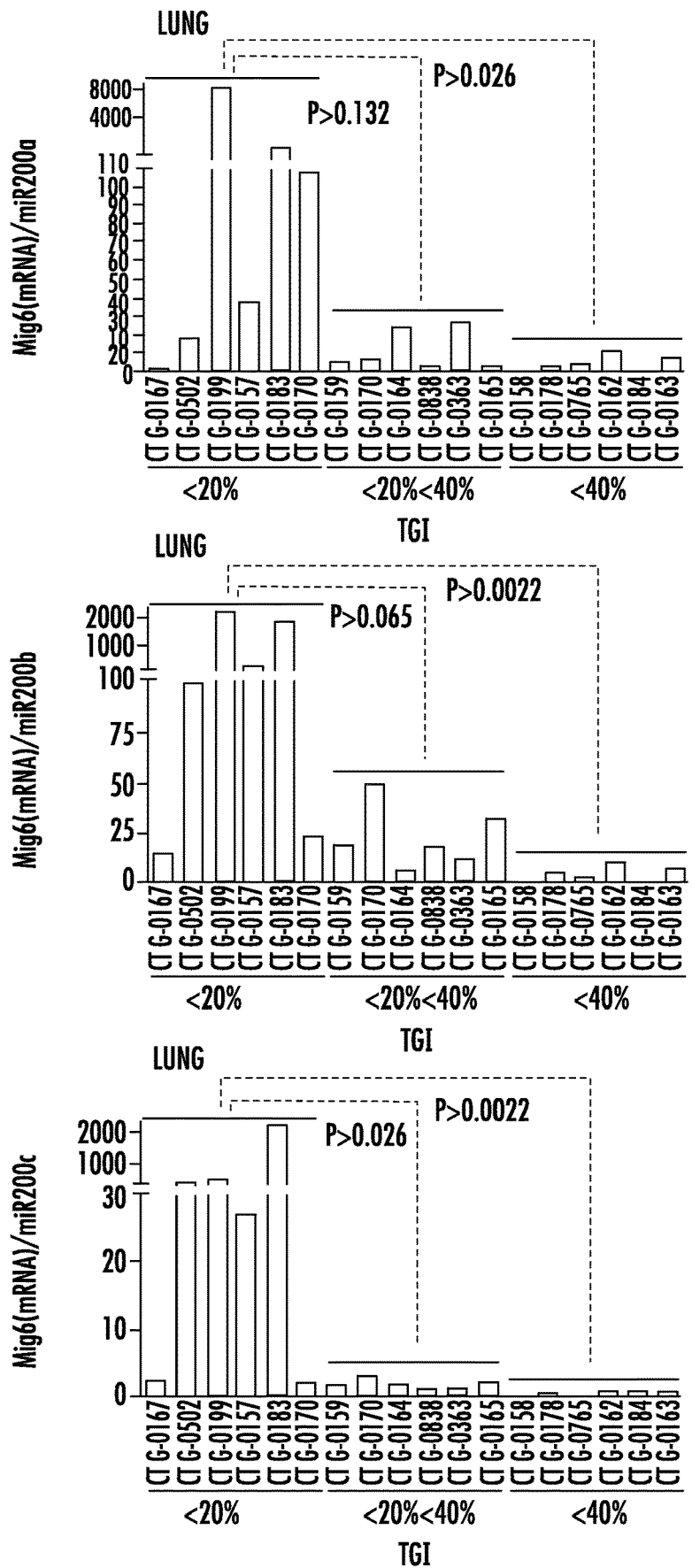
FIGS. 6A-6B show that the Mig6(mRNA)/miR200 ratio predicts response to erlotinib in directly xenografted primary human lung and pancreatic tumors. RNA was extracted from A. 18 human NSCLCs and B. 27 pancreatic directly xenografted low passage tumors. Levels of miR200 family members were measured by quantitative RT-PCR and mRNA levels of Mig6 were determined by Affymetrix expression array. The ratios of Mig6(mRNA)/miR200a, Mig6(mRNA)/miR200b and Mig6(mRNA)/miR200c were plotted against erlotinib responsiveness, with the more resistant tumors clustered to the left and the more sensitive models clustered on the right.
Figure 6B:
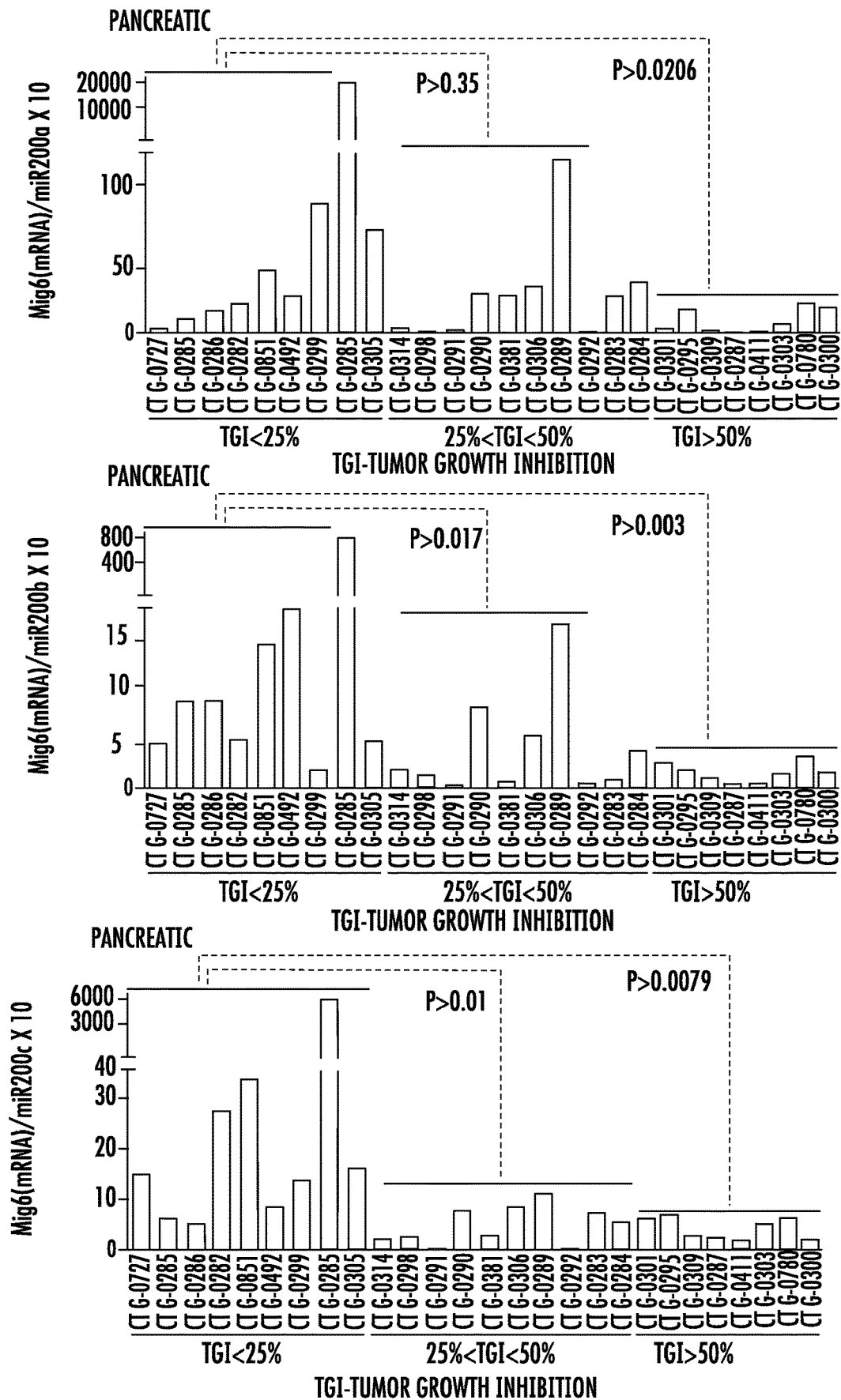

Mig6(mRNA)/miR200 ratio predicts response to erlotinib in directly xenografted primary human lung and pancreatic tumors. We obtained 18 human NSCLCs, and 27 pancreatic tumors that were directly xenografted into nude mice. Tumor characteristics, including KRAS, NRAS and p53 mutation status, are summarized in Table 1 (FIG. 8). No erlotinib-sensitizing mutations in EGFR were detected in any of these tumors and there was no correlation of KRAS mutation with erlotinib response. For all models tested, miR200 levels were measured by quantitative RT-PCR and mRNA levels of Mig6 and EGFR were determined by Affymetrix expression array. Relative tumor growth inhibition (TGI) in response to Erlotinib (35 mg/kg) was calculated as the relative tumor growth of treated mice divided by relative tumor growth of control mice (T/C). We next plotted the Mig6(mRNA)/miR200 ratio against erlotinib responsiveness, with the more resistant tumors clustered to the left and the more sensitive models clustered on the right. Lung and pancreatic tumors that display a high Mig6(mRNA)/miR200 ratio tended to cluster on the left side of the chart, indicating that they were more resistant to erlotinib (FIGS. 6A and 6B). Lung models with a TGI higher than 40% and pancreatic models with TGI greater than 50%, were associated with significantly lower Mig6(mRNA)/miR200a, Mig6(mRNA)/miR200b or Mig6(mRNA)/miR200c ratios and greater miR200 expression (FIG. 6). Our data showed that expression of miR200c (data not shown) and subsequently the Mig6(mRNA)/miR200c ratio (FIG. 6) showed the strongest correlation with erlotinib response compared to miR200b and miR200a, suggesting that miR200c might play a more dominant role in regulating Mig6. Supporting this observation, an inverse correlation between miR200c and Mig6 expression levels was noted across the pancreatic models (data not shown). In lung models, tumors with higher erlotinib sensitivity displayed a similar pattern of low Mig6(mRNA)/miR200c ratio. Of note, four erlotinib-resistant lung tumors with low EGFR and Mig6 expression (CTG-0167, CTG-0502, CTG-0199 and CTG-0157) exhibited even lower levels of miR200c (data not shown). Unlike the limited predictive ability of the Mig6/EGFR ratio in such tumors with low EGFR expression, the Mig6(mRNA)/miR200c ratio was still able to correctly identify three out of four of these lung tumors with low EGFR mRNA as erlotinib-resistant. Therefore, the ratio of Mig6 to miR200 was a reliable predictive biomarker of the primary tumors response to EGFR TKIs regardless of their EGFR status.

Figure 7:
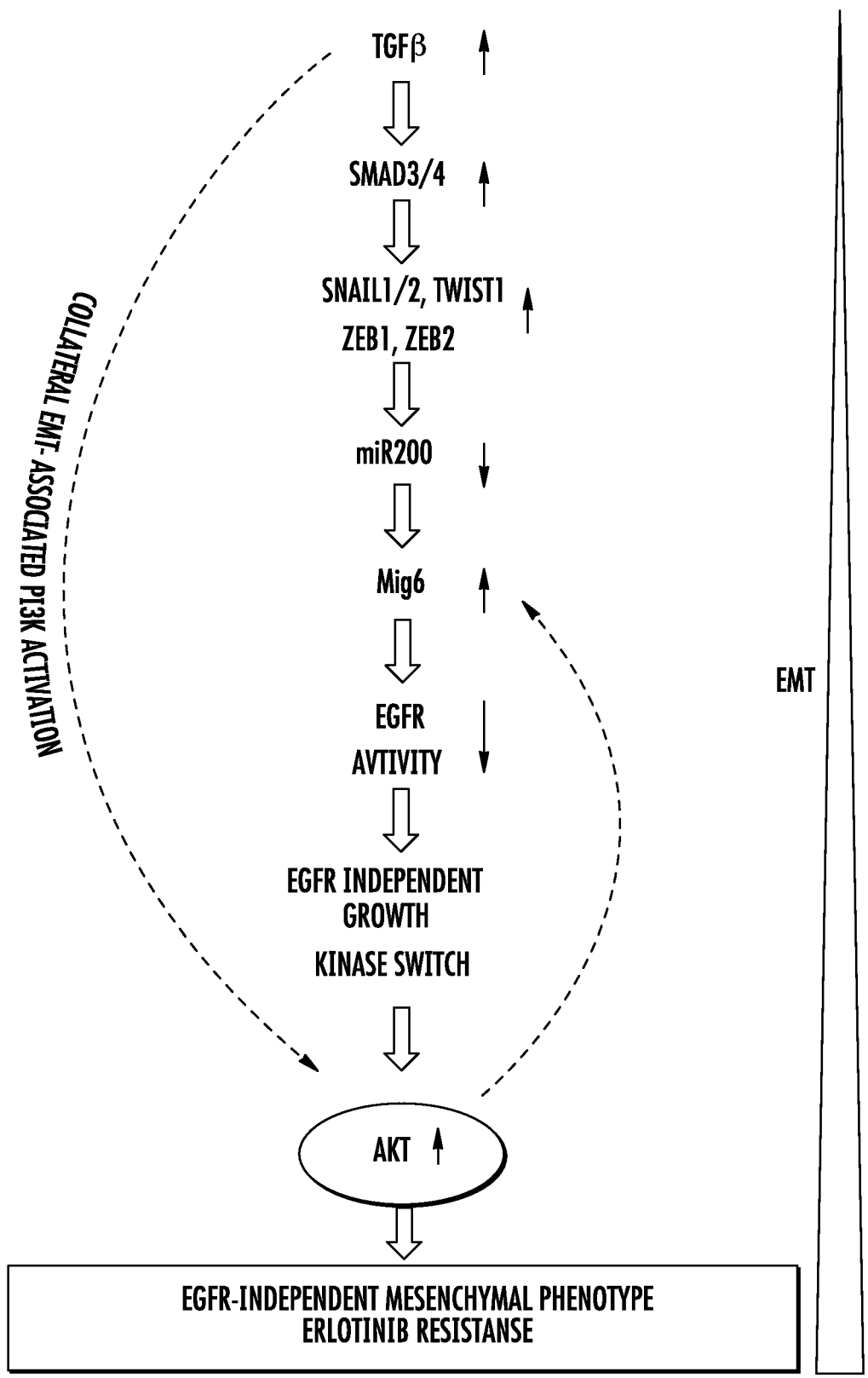
FIG. 7 is an illustration of a possible mechanism for the evolution of resistance to erlotinib.

While not being limited to any particular theory, the inventors demonstrate that the TGFβ-miR200-Mig6 network orchestrates the EMT-associated kinase switch that induces resistance to EGFR inhibitors (FIG. 7), as such, the autonomous production of TGFβ by tumor cells can be a frequent mechanism by which cancers induce an erlotinib-resistant phenotype. The present invention provides the following lines of evidence to support this conclusion. In a panel of 25 cancer cell lines of different tissue origins (H&N, bladder, and lung), erlotinib-resistant, mesenchymal-like cells produced higher levels of TGFβ than the epithelial-like, erlotinib sensitive cells, showing that increased autocrine exposure to TGFβ may be a driving force behind the erlotinib-resistant phenotype. In the same panel, resistance to erlotinib was highly correlated with EMT and an elevated Mig6/miR200c ratio. Besides the high TGFβ expression and elevated Mig6/miR200 ratio exhibited by de novo erlotinib-resistant cell lines, this phenotype was also exhibited by SCC-R tumor cells that had acquired erlotinib-resistance by culturing erlotinib-sensitive SCC-S cells in the presence of escalating concentrations of erlotinib. SCC-R cells expressed more than 10-fold higher levels of TGF-β compared with SCC-S cells, and this was associated with reduction of miR200 family members (200a, 200b, 200c and 205) and concomitant increase in Mig6 expression. Furthermore, these cells showed evidence of EMT and manifested a kinase switch involving reduced activity of the EGFR kinase family and activation of alternative RTKs (pPDGFR, pFGFR, pVEGFR, and pIGFR) and AKT. In support of the causal association of tumor cell expression of TGFβ with an elevated Mig6/miR200 ratio and erlotinib-resistance, exposure of various erlotinib-sensitive epithelial tumor cells to exogenous TGFβ resulted in their EMT-associated conversion to an erlotinib-resistant phenotype with an attendant reduction of miR200, increase in Mig6 expression, decrease in EGFR activity, and activation of AKT. Conversely, blockade of TGFβ signaling in erlotinib-resistant, mesenchymal-like cell lines resulted in a concurrent increase of miR200c and miR205 transcripts, downregulation of AKT activity and Mig6 levels, and a significant increase in erlotinib sensitivity.

The 25 H&N, bladder, and lung cancer cell lines used in the inventive methods showed an inverse correlation between the expression levels of Mig6 and miR200. Whereas erlotinib-sensitive cells displayed a low Mig6/miR200 ratio, erlotinib-resistant cells exhibited a high Mig6/miR200 ratio. Likewise, analyses of primary tumor xenografts of patient-derived lung and pancreatic cancers carrying wt-EGFR showed that the tumor Mig6(mRNA)/miR200 ratio is inversely correlated with response to erlotinib in vivo. A similar pattern was noted during TGFβ-induced EMT, wherein downregulation of miR200 family members was paralleled by upregulation of Mig6. By performing PicTar, TargetScan, miRanda and miRBase searches to predict miRNA-mRNA interactions on the Mig6 3'UTR region, it was found that the 3'UTR of Mig6 contains conserved potential binding sites for miR-200 family members. Additionally, recent work indicates that miR200c can directly bind to the 3'UTR region of Mig6 mRNA and downregulate its expression. In line with this data, the Mig6(mRNA)/miR200c ratio showed the strongest association with erlotinib sensitivity in cancer cell lines as well as primary human tumor xenografts in vivo. These data show that TGFβ-mediated suppression of the miR200 family unleashes expression of Mig6, which in turn quenches EGFR activity. The elevation of Mig6 following TGFβ-induced EMT is sustained by EGFR-independent activation of AKT since this is reduced by PI3K inhibitors, but not by erlotinib. Therefore, a high Mig6/miR200c ratio is a sequel of TGFβ-induced EMT and a signature of the EMT-associated kinase switch responsible for resistance to EGFR TKI. As such, the tumor Mig6(mRNA)/miR200c ratio has clinical value as a predictive biomarker of the differential response of tumors to EGFR TKI. The inventive methods further provide that inhibition of the molecular determinants of the EMT-associated kinase switch, such as TGFβ, may prevent or reverse tumor cell resistance to EGFR inhibitors.

The present invention provides all references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating a subject having a cancer comprising:
    a) isolating a RNA sample from a cancer cell or population of cells from the subject;
    b) performing quantitative real-time PCR on the RNA from the sample of the cancer cell or population of cells using the PCR primers and probes specific for Mig6 mRNA, and for one or more microRNAs selected from the group consisting of: miR200a, miR200b, miR200c and miR205;
    c) determining the ratio of the quantity of the Mig6 mRNA to the quantity of one or more microRNAs selected from the group consisting of: miR200a, miR200b, miR200c and miR205 in the sample of the cancer cell or population of cells and identifying the cancer of the subject as susceptible to Epidermal Growth Factor Receptor (EGFR) tyrosine kinase inhibitor (TKI) treatment when the ratio of Mig6 mRNA to the quantity of one or more microRNAs is less than or equal to 0.05; and
    d) administering to the subject an effective amount of at least one EGFR TKI.

2. The method of claim 1, wherein the at least one EGFR TKI is selected from the group consisting of axitinib, dasatinib, erlotinib, gefitinib, imatinib, lapatinib, niolinib, pazopanib, sorafenib, and sunitinib.

3. The method of claim 2, wherein the method further comprises administering to the subject an effective amount of at least one additional chemotherapeutic agent which is not a EGFR TKI.

4. The method of claim 1, wherein the method further comprises repeating steps a) to c) during treatment of the subject.

5. A method for treating a subject having a cancer comprising:
    a) isolating a RNA sample from a cancer cell or population of cells from the subject;
    b) performing quantitative real-time PCR on the RNA from the sample of the cancer cell or population of cells using the PCR primers and probes specific for Mig6 mRNA, and for one or more microRNAs selected from the group consisting of: miR200a, miR200b, miR200c and miR205;
    c) determining the ratio of the quantity of the Mig6 mRNA to the quantity of one or more microRNAs selected from the group consisting of: miR200a, miR200b, miR200c and miR205 in the sample of the cancer cell or population of cells and identifying the cancer of the subject as susceptible to TGFβ inhibitor treatment when the ratio of Mig6 mRNA to the quantity of one or more microRNAs is greater than 0.05; and
    d) administering to the subject an effective amount of at least one TGFβ inhibitor.

6. The method of claim 5, wherein the TGFβ inhibitor is selected from the group consisting of SB-431542, A-83-01, D-4476, LY-364947, GW-788388, SB-505124, or TGFβRII/Fc.

7. The method of claim 5, wherein the method further comprises repeating steps a) to c) during treatment of the subject.

* * * * *